United States Patent
Govari et al.

(10) Patent No.: US 9,638,820 B2
(45) Date of Patent: May 2, 2017

(54) CALIBRATION JIG FOR A FLAT LOCATION PAD

(71) Applicant: BIOSENSE WEBSTER (ISRAEL) LTD., Yokneam (IL)

(72) Inventors: Assaf Govari, Haifa (IL); Vadim Gliner, Haifa (IL)

(73) Assignee: Biosense Webster (ISRAEL) LTD., Yokneam (IL)

( * ) Notice: Subject to any disclaimer, the term of this patent is extended or adjusted under 35 U.S.C. 154(b) by 557 days.

(21) Appl. No.: 14/195,068

(22) Filed: Mar. 3, 2014

(65) Prior Publication Data

US 2015/0247944 A1    Sep. 3, 2015

(51) Int. Cl.
| | | |
|---|---|---|
| *G01V 3/00* | (2006.01) | |
| *G01V 3/08* | (2006.01) | |
| *G01V 3/14* | (2006.01) | |
| *A61B 5/055* | (2006.01) | |
| *A61B 5/06* | (2006.01) | |
| *G01R 33/58* | (2006.01) | |

(52) U.S. Cl.
CPC ............ *G01V 3/08* (2013.01); *A61B 5/055* (2013.01); *A61B 5/062* (2013.01); *G01R 33/58* (2013.01); *G01V 3/14* (2013.01); *Y10T 29/4902* (2015.01)

(58) Field of Classification Search
USPC ........................................................ 324/309
See application file for complete search history.

(56) References Cited

U.S. PATENT DOCUMENTS

| | | | |
|---|---|---|---|
| 6,335,617 B1 * | 1/2002 | Osadchy ................. | A61B 5/06 324/202 |
| 8,618,795 B1 * | 12/2013 | Nagarkar ........... | G01R 33/0035 252/62.3 C |
| 2007/0265526 A1 | 11/2007 | Govari et al. | |
| 2008/0079421 A1 | 4/2008 | Jensen | |
| 2008/0183064 A1 * | 7/2008 | Chandonnet ............. | A61B 5/06 600/407 |
| 2011/0200244 A1 * | 8/2011 | Ashton ................. | G01R 33/58 382/131 |
| 2012/0165656 A1 | 6/2012 | Montag et al. | |
| 2014/0005526 A1 | 1/2014 | Govari et al. | |

OTHER PUBLICATIONS

European Search Report dated May 19, 2015 for Application No. EP15157168.

\* cited by examiner

*Primary Examiner* — Rodney Fuller
(74) *Attorney, Agent, or Firm* — Louis J. Capezzuto

(57) ABSTRACT

An apparatus includes a detector assembly, a positioning unit, and interface circuitry. The detector assembly includes an array of multiple magnetic field detectors. The positioning unit is configured to fix the detector assembly at one or more known positions relative to a location pad, which generates magnetic fields for performing position measurements on an intra-body magnetic field detector using a positioning system. The interface circuitry is configured to output electrical signals that are produced by the magnetic field detectors of the detector assembly when the detector assembly is fixed at the known positions, so as to calibrate the position measurements performed by the positioning system.

19 Claims, 5 Drawing Sheets

FIG. 4A
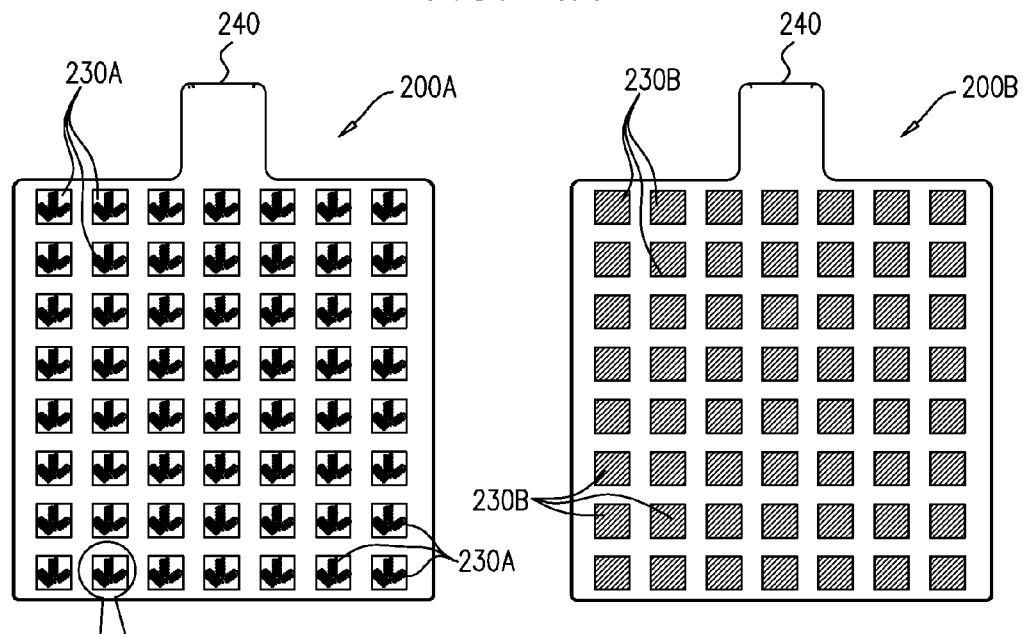
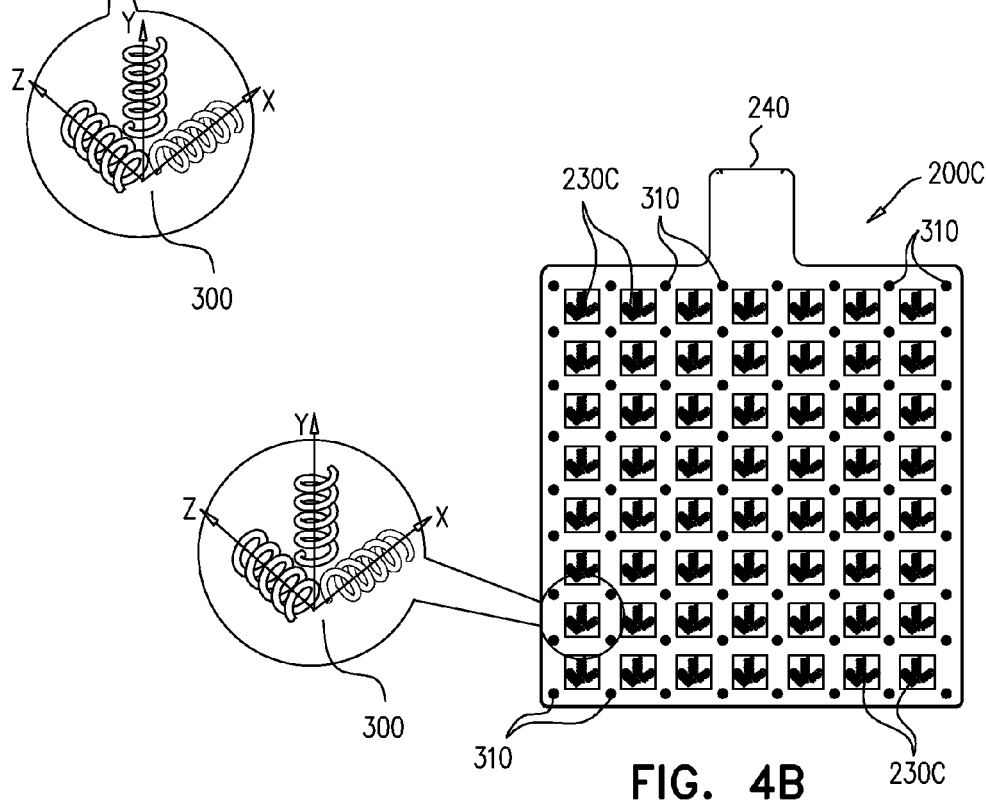
FIG. 4B

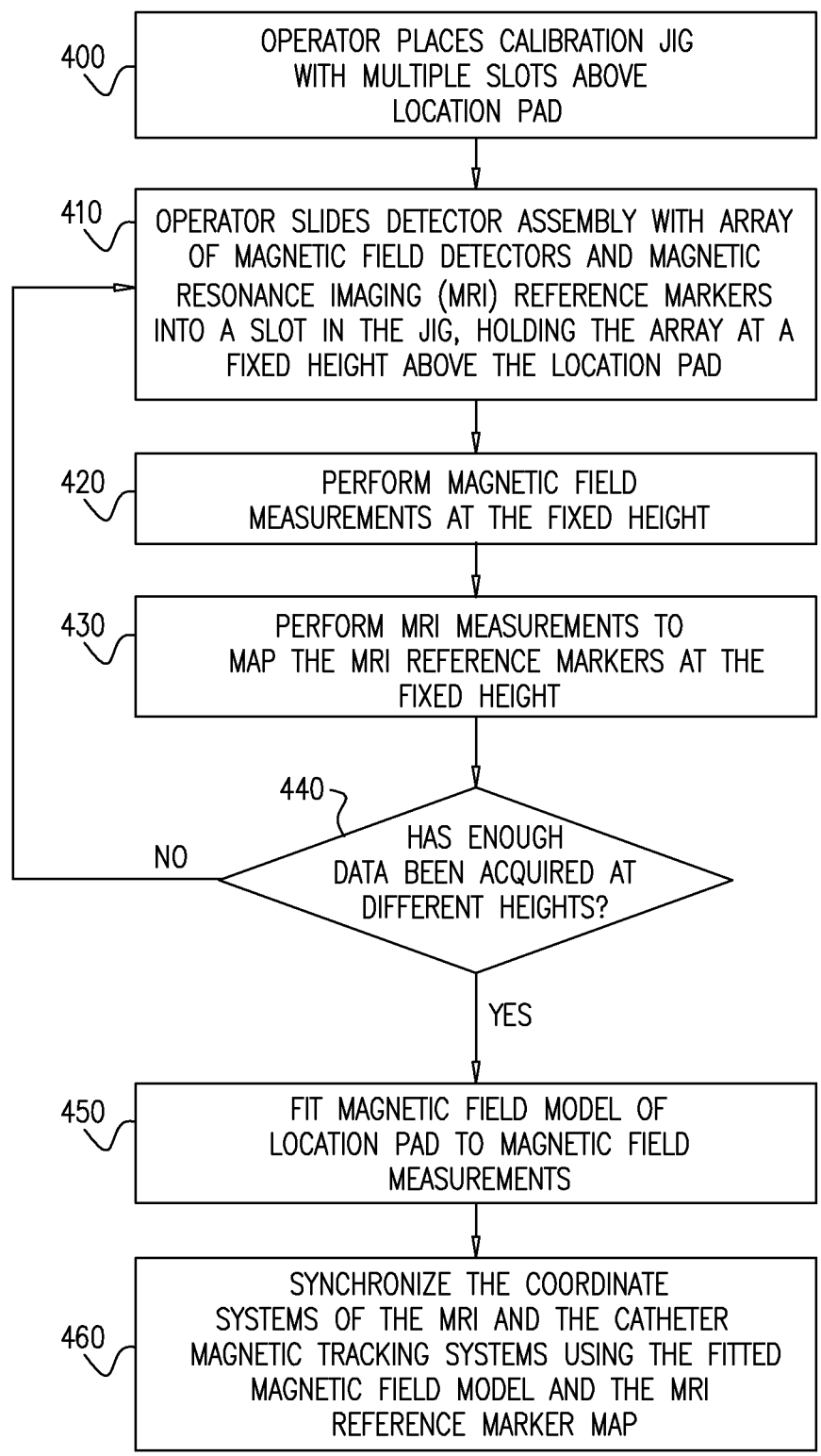

CALIBRATION JIG FOR A FLAT LOCATION PAD

FIELD OF THE INVENTION

The present invention relates generally to calibration, and particularly to methods for calibrating intra-body probe tracking systems.

BACKGROUND OF THE INVENTION

The position of an intra-body probe, such as a catheter, can be tracked in the body of a patient using magnetic position tracking techniques. For example, U.S. Patent Application Publication 2007/0265526, whose disclosure is incorporated herein by reference, describes a magnetic position tracking system for performing a medical procedure on a patient. The patient is positioned on an upper surface of a table includes a location pad, which is positioned on the upper surface of the table beneath the patient. The location pad includes one or more field generators, which are operative to generate respective magnetic fields and are arranged so that a thickness dimension of the location pad is no greater than three centimeters. A position sensor is fixed to an invasive medical device for insertion into a body of the patient, and is arranged to sense the magnetic fields so as to measure a position of the medical device in the body.

Magnetic resonance imaging (MRI) is an imaging technique used for visualizing tissue, particularly soft tissue, of a patient. The technique relies on exciting nuclei, typically hydrogen nuclei, from their equilibrium state, and measuring the resonant radio-frequency signals emitted by the nuclei as they relax back to equilibrium. The measured resonant radio-frequency signals are used to create high quality images of the tissue. Medical practitioners may use MRI in conjunction with other medical procedures.

SUMMARY OF THE INVENTION

An embodiment of the present invention provides an apparatus including a detector assembly, a positioning unit, and interface circuitry. The detector assembly includes an array of multiple magnetic field detectors. The positioning unit is configured to fix the detector assembly at one or more known positions relative to a location pad, which generates magnetic fields for performing position measurements on an intra-body magnetic field detector using a positioning system. The interface circuitry is configured to output electrical signals that are produced by the magnetic field detectors of the detector assembly when the detector assembly is fixed at the known positions, so as to calibrate the position measurements performed by the positioning system.

In some embodiments, the positioning unit includes multiple slots, which are configured to accept the detector assembly so as to fix the detector assembly at the respective known positions relative to the location pad. In other embodiments, each of the multiple magnetic field detectors includes one or more magnetic coils. In yet other embodiments, the positioning unit includes an adapter conforming to a shape of the location pad.

In some embodiments, the positioning unit includes one or more turn screws, which are configured to be rotated so as to set the known positions of the detector assembly relative to the location pad. In other embodiments, the interface circuitry includes multiple cables, connected across the multiple magnetic field detectors and placed in respective multiple channels formed in the detector assembly so as to reduce crosstalk between the multiple cables.

In some embodiments, the apparatus includes a registration array of multiple Magnetic Resonance Imaging (MRI) reference markers, and the positioning unit is further configured to fix the registration array of the MRI reference markers in at least one known position relative to the location pad, for registering coordinate systems of the positioning system and an MRI system. In other embodiments, the registration array of the MRI reference markers is comprised in a registration assembly that is separate from the detector assembly. In yet other embodiments, the registration array of the MRI reference markers is embedded in the detector assembly.

In some embodiments, the MRI reference markers include fluid-filled spheres having known radii. In other embodiments, the MRI reference markers include fluid-filled cubes having known dimensions.

There is also provided, in accordance with an embodiment of the resent invention, a method including coupling an array of multiple magnetic field detectors to a location pad, which generates magnetic fields for performing position measurements on an intra-body magnetic field detector using a positioning system. The array of the magnetic field detectors is fixed at one or more known positions relative to the location pad. The position measurements performed by the positioning system based on electrical signals, which are produced by the magnetic field detectors are calibrated when the array is fixed at the known positions.

There is also provided, in accordance with an embodiment of the resent invention, a method including forming a detector assembly, which includes an array of multiple magnetic field detectors. A positioning unit is configured to fix the detector assembly at one or more known positions relative to a location pad, which generates magnetic fields for performing position measurements on an intra-body magnetic field detector using a positioning system. Interface circuitry is configured to output electrical signals that are produced by the magnetic field detectors of the detector assembly when the detector assembly is fixed at the known positions, so as to calibrate the position measurements performed by the positioning system.

The present invention will be more fully understood from the following detailed description of the embodiments thereof, taken together with the drawings in which:

BRIEF DESCRIPTION OF THE DRAWINGS

FIGS. 4A and 4B are schematic, pictorial illustrations of detector assemblies, in accordance with embodiments of the present invention; and FIG. 5 is a flow chart that schematically illustrates a method for calibrating a location pad, and registering coordinate systems between a magnetic resonance image (MRI)

Figure 1:
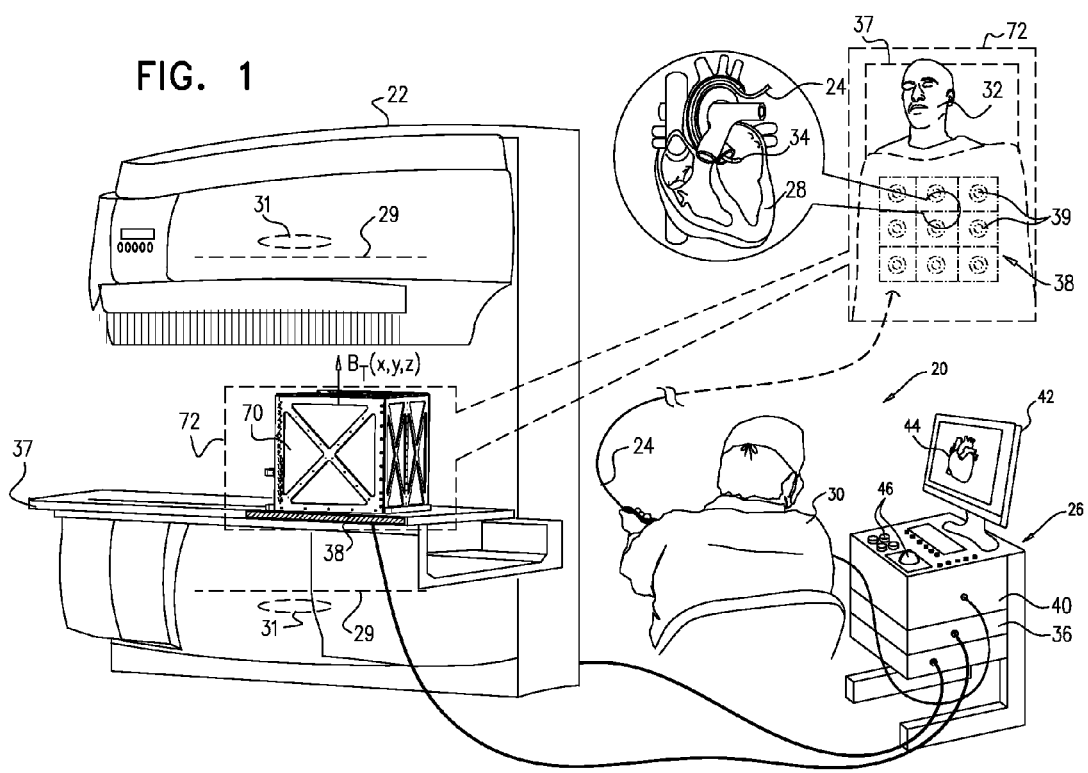
FIG. 1 is a schematic, pictorial illustration of a system for magnetic catheter tracking collocated with magnetic resonance imaging (MRI), in accordance with an embodiment of the present invention.

scanner and a magnetic catheter tracking system, in accordance with an embodiment of the present invention.

DETAILED DESCRIPTION OF EMBODIMENTS

Overview

Intra-body probes, such as catheters, are used in various therapeutic and diagnostic medical procedures. The catheter is inserted into the living body of a patient and navigated to the target region in a body cavity to perform the medical procedure. In magnetic field-based position tracking systems, an external magnetic field is applied to the patient's body. The magnetic field is produced by multiple magnetic field generators, e.g., field generating coils, typically placed in a location pad under the patient. A sensor installed near the distal end of the catheter responds to the field by producing an electric signal. The signal is then used by the tracking system to locate the position and orientation of the catheter in the patient's body.

Magnetic position tracking of the catheter is sometimes performed in or near a magnetic resonance imaging (MRI) system. Collocation of these two systems enables, for example, joint display of magnetic position tracking and MRI data. Collocation of this sort, however, presents a number of challenges. For example, the form factor of the location pad used for magnetic catheter tracking should be compatible with the MRI system. Moreover, the MRI system may distort the magnetic fields generated by the magnetic location system, and may therefore distort the position measurements.

Embodiments of the present invention that are described herein provide novel calibration jigs for calibrating the location pad in the presence of the MRI system, and for assisting in coordinate-system registration between the MRI system and the catheter magnetic positioning system. In some embodiments, a jig of this sort is placed on top of the location pad and conforms to the form factor of the MRI-compliant location pad.

In an example embodiment, the jig comprises a positioning unit having multiple slots. A detector assembly, which comprises multiple magnetic field detectors arranged in an array, is inserted alternately into the slots of the jig, thereby fixing the array at known positions relative to the location pad. The magnetic field generated by the location pad is measured by the detectors in the array while held at the various known positions. Typically, a mathematical model of the magnetic field generated by the location pad is fit to the magnetic field measurements.

In some embodiments, position control above the location pad is provided by sliding the detector assembly out of one slot in the positioning unit and into another slot to hold the detector assembly at a different height above the location pad. In this manner, when enough magnetic field data is measured at multiple spatial points around the volume where the patient torso would normally be present, the data is fit to the magnetic field model in order to calibrate the position measurements of the catheter magnetic tracking system. This process effectively compensates for distortion of the magnetic field of the location pad by the MRI system.

In other embodiments, the calibration jig further comprises a registration array of MRI reference markers, which can be imaged and mapped accurately by the MRI system. The registration array can be used for imaging the calibration jig by the MRI system, and registering the MRI image coordinate system with the coordinate system of the catheter magnetic tracking system. The MRI reference markers may comprise, for example, spheres or cubes that are filled with fluid (e.g., water) and have known dimensions. The MRI reference markers may be embedded in the detector assembly, or they may be mounted in a separate assembly that is inserted into the positioning unit.

System Description

FIG. 1 is a schematic, pictorial illustration of a system 20 for magnetic catheter tracking collocated with magnetic resonance imaging (MRI), in accordance with an embodiment of the present invention. System 20 comprises an MRI scanner 22, an intra-body probe 24, such as a catheter, and a control console 26.

An operator 30, such as a cardiologist, percutaneously navigates catheter 24 through the vascular system of a patient 32 so that a distal end 34 of the catheter 24 enters a body cavity, herein assumed to be the cardiac chamber. Catheter 24 may be used, for example, for mapping electrical potentials in a chamber of a heart 28 of patient 32 with multiple electrodes disposed near distal end 34 of catheter 24 that contact the tissue of the heart cavity at multiple points. In alternative embodiments, catheter 24 may be used, mutatis mutandis, for other therapeutic and/or diagnostic functions in the heart or other body organs.

Console 26 uses magnetic position sensing to determine the orientation and position coordinates of distal end 34 of catheter 24 inside heart 28. Console 26 operates a driver circuit 36 that drives one or more magnetic field generators 39 in a location pad 38 below the patient's torso on a table 37 as shown in a dotted inset 72 in the upper right hand corner of FIG. 1. A position sensor installed in distal end 34 generates electrical signals in response to the magnetic fields generated by location pad 38, thereby enabling console 26 to determine the position and orientation of distal end 34 with respect to location pad 38, and thus, the position and orientation within the heart of patient 32.

MRI scanner 22 comprises magnetic field coils 29, including field gradient coils, which together generate a spatially variant magnetic field. The spatially variant magnetic field provides spatial localization for radio frequency (RF) signals generated by the scanner. In addition, the scanner comprises transmit/receive coils 31. In a transmit mode, coils 31 radiate RF energy to patient 32, the RF energy interacting with the nuclear spins of the patient's tissue and thereby realigning the magnetic moments of the nuclei away from their equilibrium positions. In a receive mode, coils 31 detect RF signals received from the patient's tissue as the tissue nuclei relax to their equilibrium state.

FIG. 1 shows table 37 in MRI scanner 22 which supports patient 32 as shown in dotted region 72 in the upper right hand corner of FIG. 1. In the embodiments described herein, a calibration jig 70 is used for calibrating system 20. Jig 70 is placed on table 37 above location pad 38 within MRI scanner 22 in the same region where the torso of patient 37 would normally be positioned on table 37 as shown the upper right inset. In this region, calibration jig 70 is used to calibrate the total magnetic field $B_T(x,y,z)$ created by location pad 38. In other embodiments, jig 70 is also used to register the coordinate system of MRI scanner 22 with the coordinate system of the magnetic catheter tracking system, as will be described further below.

A processor 40 has multiple functions in the embodiment shown in FIG. 1. First, processor 40 is configured to receive electrical signals induced in the position sensor at catheter distal end 34 in response to the magnetic field generated by location pad 38 via interface circuitry (not shown). Processor 40 uses the received electrical signals to locate the catheter in the patient's body. In some embodiments, the interface circuitry is also configured to receive respective multiple electrical signals from multiple magnetic detectors installed in calibration jig 70 measuring $B_T(x,y,z)$. These multiple electrical signals are relayed to processor 40 via the interface circuitry. Processor 40 uses these signals for position calibration as will be explained later.

Secondly, processor 40 operates MRI scanner 22 by using circuitry to control MRI coils 29, including forming required magnetic field gradients, as well as other circuitry to operate transmit/receive coils 31 around patient 32. Processor 40 acquires MRI data of heart 28 of patient 32, or at least of the cardiac chamber to be imaged, using signals received by coils 31. Using the data, processor 40 displays an image 44 of heart 28 to operator 30 on a display 42. The position of the catheter acquired by the magnetic tracking system can be super-imposed on image 44 of heart 28 on display 42 acquired by MRI scanner 22. In yet other embodiments, operator 30 can manipulate image 44 using one or more input devices 46.

Alternatively, the functions of processor 40 may be split between two processors, one managing the magnetic position tracking system and one managing the MRI scanner. Processor 40 may also be configured to reduce magnetic interference, or coexistence effects of the respective MRI system and magnetic catheter tracking systems, which may, for example, degrade system performance. Stated differently, processor 40 is configured to compensate for coupling effects, for example, between the magnetic fields generated by MRI coils 29 and 31 used in MRI scanner 22, and the magnetic generators 39 in location pad 38 for the magnetic catheter tracking system.

Processor 40 typically comprises a general-purpose computer, which is programmed in software to carry out the functions that are described herein. The software may be downloaded to processor 40 in electronic form, over a network, for example, or it may be provided on non-transitory tangible media, such as optical, magnetic or electronic memory media. Alternatively, some or all of the functions of processor 40 may be carried out by dedicated or programmable digital hardware components, or by using a combination of hardware and software elements.

The magnetic catheter tracking system can be realized as the CARTO XP EP Navigation and Ablation System, available from Biosense Webster, Inc. (Diamond Bar, Calif.), suitably modified to execute the procedures described herein.

The embodiments shown in FIG. 1 are merely for conceptual clarity, and not by way of limitation of the embodiments of the present invention. MRI scanner 22 and the magnetic catheter tracking system may have separate processors for each system and not shared as in the embodiment shown in system 20. Single or separate displays may be used for the MRI scanner and the catheter tracking system.

MRI Compatible Location Pad

Figure 2:
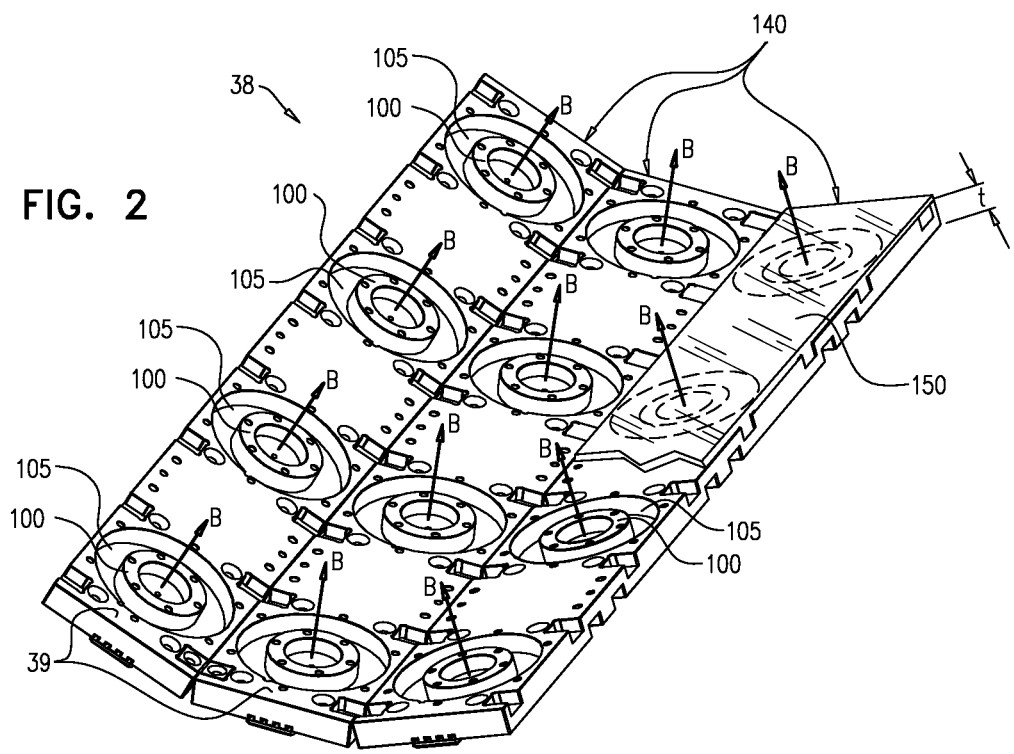
FIG. 2 is a schematic, pictorial illustration of a location pad, in accordance with an embodiment of the present invention.

FIG. 2 is a schematic, pictorial illustration of location pad 38, in accordance with an embodiment of the present invention. The location pad has a low profile, and can be easily placed under the patient. The location pad is slightly curved, i.e., deviates slightly from a flat plane, for example to fit into the chamber of MRI scanner 22. Additional aspects of low-profile location pads such as pad 38 are described in U.S. patent application Ser. No. 14/138,654, entitled "Low-profile location pad for magnetic-based intra-body probe tracking system," whose disclosure is incorporated herein by reference.

Location pad 38 comprises multiple magnetic field generators 39 arranged in an array. Twelve generators 39 of equal sizes are shown in the exemplary embodiment of FIG. 2. The array is held in a housing which may be made from any suitable material, such as from various plastics.

Each generator 39 comprises a planar coil 100. The coil may be formed from any suitable material, such as copper. When a signal, typically a current, is applied to coil 100, coil 100 generates a magnetic field B oriented in response to the applied signal and perpendicular to the plane of the coil. Each row 140 of coils 100 is planar, but the rows lie on a slightly curved surface. In this configuration, too, the axes of the magnetic fields generated by coils 100 are perpendicular to the surface of the location pad. On the right-most row shown in the FIG. 2, magnetic field generators 39 have a lid 150 covering coils 100, which may be formed from any suitable material, such as a plastic, covering the entire array.

When patient 32 lies on location pad 38 as shown in dotted region 72 in the upper right hand corner of FIG. 1 and catheter 24 is navigated in the patient's body above the location pad, a magnetic sensor coil 120 near distal end 34 of the catheter generates an electrical signal, typically a voltage, in response to the composite magnetic field $B_T(x,y,z)$ shown in FIG. 1. Processor 40 uses the generated electric signal to identify the position of distal end 34 relative to location pad 38 and thus, the position in patient 32.

In the embodiments presented herein, the location pad is configured to be placed between the patient and the top surface of table 37, e.g., with the patient lying on top of the location pad. The transverse dimensions of the location pad are typically confined to the transverse dimensions of patient table 37, which is moved into the MRI scanner. The thickness t of the location pad is usually configured to be no more than 5 mm. In this manner, the MRI scanner does not collide or interfere with location pad 38 of the magnetic tracking system, or vice versa.

Field generators 39 in location pad 38 are driven with Alternating-Current (AC) drive signals having different frequencies, such that the signals induced in the sensor at the catheter distal end can be distinguished from one another by processor 40. The use of field generators having parallel axes facilitates the mathematical modeling of the resulting magnetic field, which simplifies the computation of the position and orientation of the distal end of the catheter based on the catheter sensor output. However, the magnetic fields B generated by coils 100 are nearly parallel to one another. Any small deviations of the magnetic fields B from parallelism due to the curvature as shown in FIG. 2 were found to have a negligible impact on the accuracy of the catheter position tracking system.

Processor 40 estimates the probe position (e.g., distal end 34) in a two-stage process. In the first stage, the height of the probe above the location pad is estimated from the absolute magnitude of the composite signal $B_T(x,y,z)$ sensed by the position sensor in the probe. Then, the transverse position of the probe relative to the location pad can be determined by analyzing the relative amplitudes of the different frequencies in the composite signal. This initial estimate can be output per-se, or it can be used as the starting point to a more accurate, iterative position estimation process.

However, the two-stage process described above for estimating the position of distal end 34 assumes that the magnetic field generated by location pad 38 in the region of the patient's torso (as shown in the inset of FIG. 1) is properly modeled and calibrated. In order to calibrate the magnetic field, any suitable mathematical model representing the magnetic field in the region above location pad 38 is fit to magnetic field measurement data acquired at different spatial points above the location pad typically in region 72 on table 37 by calibration jig 70 described herein.

Example Calibration Jig Configuration

Figure 3:
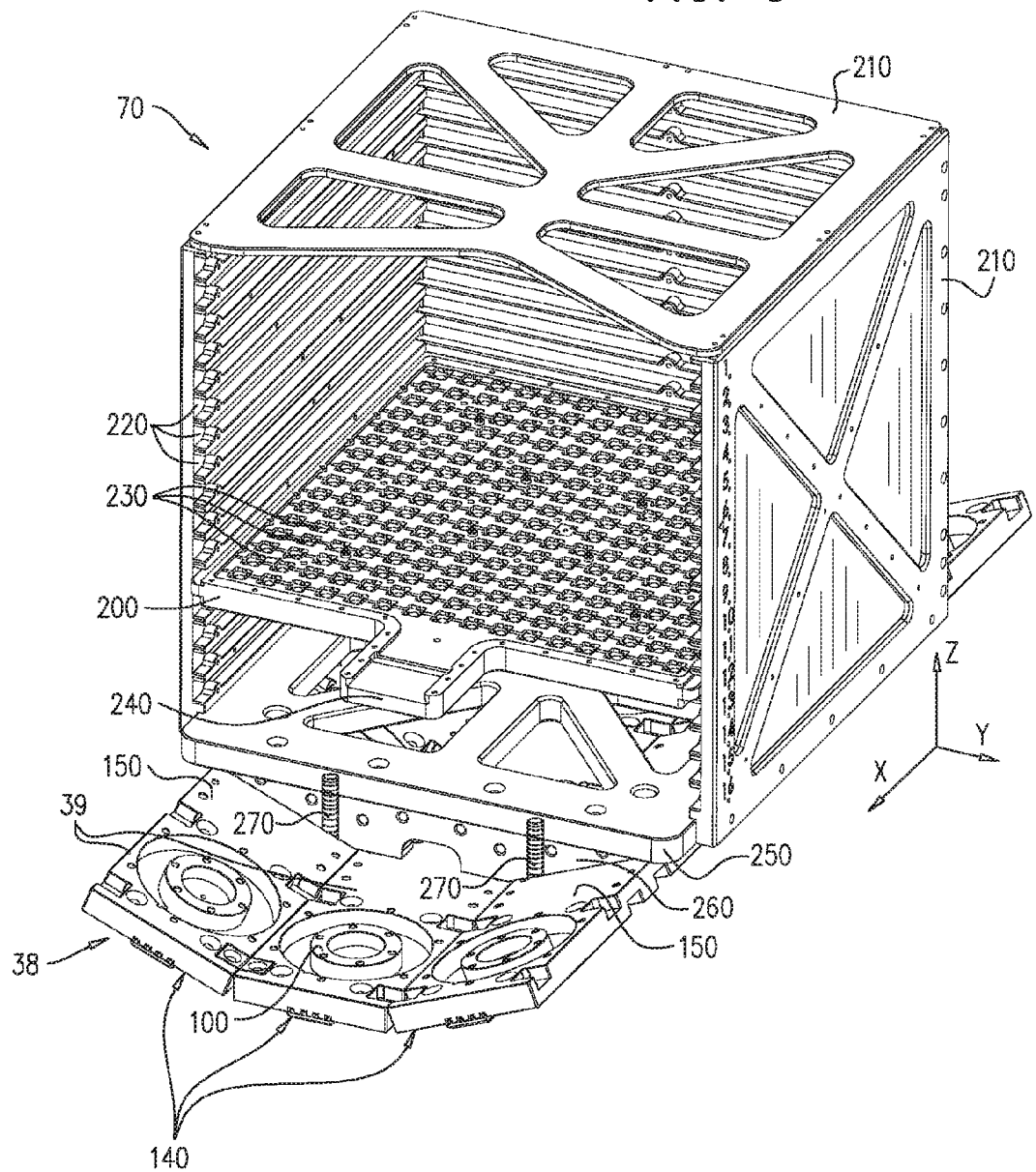
FIG. 3 is a schematic, pictorial illustration of a calibration jig, in accordance with an embodiment of the present invention.

FIG. 3 is a schematic, pictorial illustration of calibration jig 70, in accordance with an embodiment of the present invention. Calibration jig 70 comprises a positioning unit 210 having multiple slots 220 that are separated by a fixed, predefined distance between adjacent slots. Jig 70 is placed above location pad 38, as shown in FIG. 1.

A detector assembly 200, also referred to as a shelf, comprises an array of multiple magnetic field detectors 230. Detector assembly 200 can be inserted into any of slots 220 in positioning unit 210. The multiple slots in positioning unit 210 are configured to fix detector assembly 200 at one or more known positions relative to location pad 38. In the embodiment shown in FIG. 3, the multiple slots control the position (e.g., the height) of the detector array above the location pad.

In order to model the magnetic field generated by location pad 38 within the region where the torso of patient 32 would be located during the medical procedure, detectors 230 measure the magnetic field (e.g., complex field vector including magnitude and direction) at multiple respective points within the volume of the patient torso (e.g., dotted region 72). Detectors 230 in the planar array in detector assembly 200 measure the field in the X-Y plane as shown. However, to measure the distribution as a function of height, operator 30 changes the height of the array of detectors 230 above location pad 38 in the Z-direction. In the embodiment shown here, operator 30 manually slides shelf 200 out of the current slot by pulling a handle 240 and inserts shelf 200 into a different slot 220, which changes the height above location pad 38 in the Z-direction.

A baseplate 250 of positioning unit 210 is connected to a conformal adapter 260, which is configured to fit and conform to the shape of location pad 38 such that the array of detectors 230 will be in the X-Y plane at a fixed distance above the location pad and orthogonal to the Z-axis. Adapter 260 may be machined, or formed, by any suitable process so as to conform to the curvature of location pad 38.

Typical dimensions of calibration jig 70 shown in FIG. 3 are as follows. Positioning unit 210 has a depth of 370 mm (along the X-axis), width 370 mm (along the Y-axis) and a height of 350 mm (along the Z-axis). The distance between adjacent slots 220 is 20 mm. The thickness of shelf 200 is 17.5 mm. On shelf 200, the pitch of adjacent detectors 230 is 30 mm. The dimension of individual square detectors 230 shown in FIG. 3 is 15 mm. The numerical values above are given purely by way of example. In alternative embodiments, any other suitable dimensions can be used.

In some embodiments, multiple detectors 230 in detector assembly 200 are connected to processor 40 via interface circuitry that also comprises multiple cables connected across detectors 230. The interface circuitry may be located in jig 70, console 26, or in any other suitable component of system 20. The interface circuitry is configured to output the electrical signals to processor 40 (as described previously) that are produced by the magnetic field detectors in detector assembly 200 when the assembly is fixed at a known position relative to location pad 38.

In other embodiments, to avoid crosstalk between the cabling from multiple detectors 230, channels are formed, drilled or machined into the plate forming shelf 200 in which the multiple cables are placed so as to isolate the multiple cabling from multiple detectors 230 to the interface circuitry and to prevent crosstalk. Twisted pair cabling may also be used. Clips may be added to the channels to facilitate sensor removal and replacement. Processor 40 is configured to receive the magnetic field measurements from the interface circuitry measured by the multiple magnetic detectors.

The configuration of jig 70 shown in FIG. 3 is depicted purely for conceptual clarity and not by way of limitations of the embodiments of the present invention. Any other suitable dimensions of positioning unit 210, assembly 200, the pitch and size of detectors 230 may be used to realize jig 70. The positioning unit can be realized by any suitable method instead of manually changing the known positions of the detector assembly. For example, the shelf position relative to the location pad can be continuously varied by a motorized X-Y-Z axis controller.

Registration of Magnetic Catheter Tracking and MRI Coordinate Systems

When the magnetic tracking system using location pad 38 is collocated with MRI scanner 22 as shown in FIG. 1, jig 70 can be configured to facilitate the registration of the MRI coordinate system with the coordinate system of the magnetic tracking system.

FIG. 4A is a schematic, pictorial illustration of detector assembly 200, in accordance with an embodiment of the present invention. In a first exemplary embodiment, a detector assembly 200A comprises a 7×8 array of magnetic detectors 230A as shown in the left figure of FIG. 4A. Each magnetic detector 230A is realized by three magnetic coils 300 respectively oriented along three orthogonal XYZ axes. As mentioned previously, assembly 200A is not detectable by MRI scanner 22. (In alternative embodiments, each magnetic detector may comprise one or more coils.)

In an embodiment, a registration assembly 200B is fabricated with similar mechanical dimensions and footprint to detector assembly 220A. However, in place of cube-shaped holes in which magnetic detectors 230A are installed, the registration assembly comprises a 7×8 array of fluid-filled cubes 230B. Cubes 230B are filled with an MRI-detectable fluid, such as water, and serve as MRI image reference markers. The fluid is sealed in the volume of cubes 230B by any suitable procedure.

When registration assembly 200B is placed in positioning unit 210, MRI scanner 22 can then image the water-filled registration array of cubes 230B and processor 40 registers the known positions of the MRI reference markers in system 20 relative to location pad 38. The known positions of MRI reference markers 230B are then used to register the coordinate systems of the MRI system with the positioning system. Stated differently, processor 40 uses the registration array of multiple MRI reference markers 230B fixed by the positioning unit in at least one known position relative to location pad 38 for registering the coordinate systems.

FIG. 4B is a schematic, pictorial illustration of a combined detector and registration assembly 200C, in accordance with an embodiment of the present invention. Assembly 200C comprises a registration array of MRI reference markers 310. In the present example, markers 310 comprise MRI-detectible fluid-filled spheres with known radii. The registration array with markers 310 is embedded in the detector array of magnetic detectors 230C, each with three magnetic coils 300 respectively oriented along three XYZ orthogonal axes.

The mechanical footprint of assembly 200C with the distance between detectors 230C and markers 310 is also stored in memory in system 20. In this manner, MRI scanner 22 images the registration array of MRI image marker, and system 20 measures the magnetic field from location pad 38 using assembly 200C. Processor 40 stores the MRI reference marker positions and the magnetic field measurements at different positions above location pad 38 in the magnetic tracking system. In some embodiments, the assembly footprint can be applied so as to resolve the geometric differences between detectors 230C and MRI markers 230. Processor 40 then registers and synchronizes the two coordinate systems.

With reference to FIG. 4B, if N is an integer number of MRI markers 310 on shelf 200C, the error in registering the map of MRI reference markers to the coordinate system of MRI scanner 22 is proportional to $1/\sqrt{N}$. Hence, more MRI reference markers 310 distributed across the plane of shelf 200C increases the registration accuracy.

For the embodiment shown in FIG. 3 with the typical dimensions previously stated, calibration jig 70 provides a resolution of MRI scanner 22 of about 2 cm³. In other embodiments, to improve the resolution to below 1 cm³, the positioning unit can be configured to continuously vary the known position of the assembly within the separation distance between adjacent slots 220 so as to continuously fine tune the height in the Z-direction as shown in FIG. 3, after the assembly is fixed in a particular slot. For example, one or more turn screws 270 can be embedded in conformal adaptor 260 oriented in the Z-direction such that rotating the turn screws 270 essentially moves, or jacks up, baseplate 250, and thus, positioning unit 210 relative to conformal adapter 260.

In an example embodiment, each rotation of the one or more turn screws moves the entire jig 70 in the z-direction by 1 mm relative to the location pad. Thus, to achieve 1 cm³ resolution for MRI scanner, shelf 200 is inserted into chosen slot 220, an MRI scan is taken and the turn screw 270 can be rotated 10 turns up or down to change the height ±1 cm, respectively.

When moving shelf 200 to a different slot 220, jig 70 and/or location pad 38 may move on table 37 and/or relative to one another. This movement reduces the accuracy of the registration of the MRI and the location pad coordinate systems in system 20. In some embodiments, to prevent this translation, jig 70 and location pad 38 are fixed to MRI scanner 22 and/or to table 37 by any suitable method.

The embodiments shown in FIGS. 4A and 4B are depicted merely for conceptual clarity and not by way of limitation of the embodiments of the present invention. The exemplary detector and registration arrays shown may comprise any suitable number of magnetic detectors and/or MRI markers having any suitable configuration and size. The MRI reference markers may comprise any suitable MRI-detectable fluid or material.

FIG. 5 is a flow chart that schematically illustrates a method for calibrating location pad 38, and registering the coordinate systems of MRI scanner 22 and the magnetic catheter tracking system, in accordance with an embodiment of the present invention. In the present example, both functions (calibration and registration) are performed at the same time. Alternatively, however, calibration and registration may be performed separately.

In a placing step 400, operator 30 places calibration jig 70 above location pad 38 on table 37. In an insertion step 410, operator 30 inserts detector assembly 200C with an array of magnetic detectors 230C and MRI image reference markers 310 into slot 220 in jig 70, holding the array at a fixed height above location pad 38. Operator 30 activates driver circuit 36 to drive multiple magnetic field generators 39 in location pad 38. In a magnetic measurement step 420, processor 40 performs magnetic measurements at the fixed height using detectors 230C. In an MRI scanning step 430, MRI scanner 22 performs MRI measurements to map MRI reference markers 310 at the fixed height.

In a decision step 440, processor 40 assesses whether sufficient MRI and magnetic measurement data have been taken at different fixed heights. If not, the operator changes the fixed height of assembly 200C in step 410. If yes, in a fitting step 450, processor 40 fits the magnetic field model of location pad 38 to the magnetic field measurements. In a registration step 460, processor 40 synchronizes the coordinate systems of MRI scanner 22 and the catheter magnetic tracking system using the MRI reference markers imaged by the MRI scanner. In some embodiments, the mechanical footprint of assembly 200C is applied in step 460 as previously mentioned.

Although the embodiments described herein mainly address cardiac catheter tracking, the methods and systems described herein can also be used in other applications using a location pad such as in otolaryngology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:
1. An apparatus, comprising:
a detector assembly, comprising an array of multiple magnetic field detectors;
a positioning unit, which is configured to fix the detector assembly at one or more known positions relative to a location pad, which generates magnetic fields for performing position measurements on an intra-body magnetic field detector using a positioning system; and
interface circuitry, which is configured to output electrical signals that are produced by the magnetic field detectors of the detector assembly when the detector assembly is fixed at the known positions, so as to calibrate the position measurements performed by the positioning system;
wherein the positioning unit comprises at least one of:
multiple slots, which are configured to accept the detector assembly so as to fix the detector assembly at the respective known positions relative to the location pad; or
an adapter conforming to a shape of the location pad; or one or more turn screws, which are configured to be rotated so as to set the known positions of the detector assembly relative to the location pad.

2. The apparatus according to claim 1, wherein each of the multiple magnetic field detectors comprises one or more magnetic coils.

3. An apparatus, comprising:
a detector assembly, comprising an array of multiple magnetic field detectors;
a positioning unit, which is configured to fix the detector assembly at one or more known positions relative to a location pad, which generates magnetic fields for performing position measurements on an intra-body magnetic field detector using a positioning system; interface circuitry, which is configured to output electrical signals that are produced by the magnetic field detectors of the detector assembly when the detector assembly is fixed at the known positions, so as to calibrate the position measurements performed by the positioning system; and
a registration array of multiple Magnetic Resonance Imaging (MRI) reference markers, wherein the positioning unit is further configured to fix the registration array of the MRI reference markers in at least one known position relative to the location pad, for registering coordinate systems of the positioning system and an MRI system.

4. The apparatus according to claim 3, wherein the registration array of the MRI reference markers is comprised in a registration assembly that is separate from the detector assembly.

5. The apparatus according to claim 3, wherein the registration array of the MRI reference markers is embedded in the detector assembly.

6. The apparatus according to claim 3, wherein the MRI reference markers comprise fluid-filled spheres having known radii.

7. The apparatus according to claim 3, wherein the MRI reference markers comprise fluid-filled cubes having known dimensions.

8. An apparatus, comprising:
a detector assembly, comprising an array of multiple magnetic field detectors;
a positioning unit, which is configured to fix the detector assembly at one or more known positions relative to a location pad, which generates magnetic fields for performing position measurements on an intra-body magnetic field detector using a positioning system; and
interface circuitry, which is configured to output electrical signals that are produced by the magnetic field detectors of the detector assembly when the detector assembly is fixed at the known positions, so as to calibrate the position measurements performed by the positioning system;
wherein the interface circuitry comprises multiple cables, connected across the multiple magnetic field detectors and placed in respective multiple channels formed in the detector assembly so as to reduce crosstalk between the multiple cables.

9. A method, comprising:
coupling an array of multiple magnetic field detectors to a location pad, which generates magnetic fields for performing position measurements on an intra-body magnetic field detector using a positioning system;
fixing the array of the magnetic field detectors at one or more known positions relative to the location pad; and
calibrating the position measurements performed by the positioning system based on electrical signals, which are produced by the magnetic field detectors when the array is fixed at the known positions;
wherein coupling the array comprises at least one of:
coupling to the location pad a positioning unit that comprises multiple slots, and wherein fixing the array comprises inserting the array alternately into the slots so as to fix the array at the respective known positions relative to the location pad; or
coupling to the location pad an adapter conforming to a shape of the location pad.

10. The method according to claim 9, wherein each of the multiple magnetic field detectors comprises one or more magnetic coils.

11. A method, comprising:
coupling an array of multiple magnetic field detectors to a location pad, which generates magnetic fields for performing position measurements on an intra-body magnetic field detector using a positioning system;
fixing the array of the magnetic field detectors at one or more known positions relative to the location pad; and
calibrating the position measurements performed by the positioning system based on electrical signals, which are produced by the magnetic field detectors when the array is fixed at the known positions;
wherein fixing the array comprises rotating one or more turn screws, so as to set the known positions of the array relative to the location pad.

12. A method, comprising:
coupling an array of multiple magnetic field detectors to a location pad, which generates magnetic fields for performing position measurements on an intra-body magnetic field detector using a positioning system;
fixing the array of the magnetic field detectors at one or more known positions relative to the location pad;
calibrating the position measurements performed by the positioning system based on electrical signals, which are produced by the magnetic field detectors when the array is fixed at the known positions; and
coupling to the location pad a registration array of multiple Magnetic Resonance Imaging (MRI) reference markers, fixing the registration array of the MRI reference markers in at least one known position relative to the location pad, and registering coordinate systems of the positioning system and an MRI system using the registration array.

13. The method according to claim 12, wherein the registration array of the MRI reference markers is comprised in a registration assembly, which is separate from a detector assembly that comprises the magnetic field detectors.

14. The method according to claim 12, wherein the registration array of the MRI reference markers is embedded in a same assembly as the magnetic field detectors.

15. The method according to claim 12, wherein the MRI reference markers comprise fluid-filled spheres having known radii.

16. The method according to claim 12, wherein the MRI reference markers comprise fluid-filled cubes having known dimensions.

17. A method, comprising:
forming a detector assembly, comprising an array of multiple magnetic field detectors;
configuring a positioning unit to fix the detector assembly at one or more known positions relative to a location pad, which generates magnetic fields for performing position measurements on an intra-body magnetic field detector using a positioning system; and configuring interface circuitry to output electrical signals that are produced by the magnetic field detectors of the detector assembly when the detector assembly is fixed at the known positions, so as to calibrate the position measurements performed by the positioning system;

wherein the positioning unit comprises at least one of:

multiple slots, which are configured to accept the detector assembly so as to fix the detector assembly at the respective known positions relative to the location pad; or an adapter conforming to a shape of the location pad; or one or more turn screws, which are configured to be rotated so as to set the known positions of the detector assembly relative to the location pad a plurality of slots.

18. A method, comprising:

forming a detector assembly, comprising an array of multiple magnetic field detectors;

configuring a positioning unit to fix the detector assembly at one or more known positions relative to a location pad, which generates magnetic fields for performing position measurements on an intra-body magnetic field detector using a positioning system;

configuring interface circuitry to output electrical signals that are produced by the magnetic field detectors of the detector assembly when the detector assembly is fixed at the known positions, so as to calibrate the position measurements performed by the positioning system; and providing a registration array of multiple Magnetic Resonance Imaging (MRI) reference markers and configuring the positioning unit to fix the registration array of the MRI reference markers in at least one known position relative to the location pad, for registering coordinate systems of the positioning system and an MRI system.

19. A method, comprising:

forming a detector assembly, comprising an array of multiple magnetic field detectors;

configuring a positioning unit to fix the detector assembly at one or more known positions relative to a location pad, which generates magnetic fields for performing position measurements on an intra-body magnetic field detector using a positioning system;

configuring interface circuitry to:

output electrical signals that are produced by the magnetic field detectors of the detector assembly when the detector assembly is fixed at the known positions, so as to calibrate the position measurements performed by the positioning system, and place multiple cables connected across the multiple magnetic field detectors in respective multiple channels formed in the detector assembly so as to reduce crosstalk between the multiple cables.

* * * * *